United States Patent
Kachanov et al.

(10) Patent No.: US 7,535,573 B2
(45) Date of Patent: May 19, 2009

(54) CAVITY ENHANCED OPTICAL SPECTROSCOPY WITH A CAVITY HAVING A PREDETERMINED DEVIATION FROM A MODE DEGENERACY CONDITION

(75) Inventors: Alexander Kachanov, Sunnyvale, CA (US); Serguei Koulikov, Mountain View, CA (US); Bruce A. Richman, Sunnyvale, CA (US)

(73) Assignee: Picarro, Inc., Sunnyvale, CA (US)

( * ) Notice: Subject to any disclaimer, the term of this patent is extended or adjusted under 35 U.S.C. 154(b) by 78 days.

(21) Appl. No.: 11/710,029

(22) Filed: Feb. 22, 2007

(65) Prior Publication Data
US 2007/0195319 A1 Aug. 23, 2007

Related U.S. Application Data

(60) Provisional application No. 60/776,396, filed on Feb. 23, 2006.

(51) Int. Cl.
*G01B 9/02* (2006.01)
(52) U.S. Cl. .................................. 356/454; 356/437
(58) Field of Classification Search ......... 356/451–456, 356/519, 432–437, 73
See application file for complete search history.

(56) References Cited

U.S. PATENT DOCUMENTS 4,519,708 A * 5/1985 Perlmutter et al. .......... 356/467
6,084,682 A * 7/2000 Zare et al. ................... 356/437

OTHER PUBLICATIONS

Lee, D.H. et al. "Optimization of the mode matching in pulsed cavity ringdown spectroscopy by monitoring non-degenerate transverse mode beating," Mar. 14, 2002. vol. 74, pp. 435-440. Applied Physics B.

* cited by examiner

*Primary Examiner*—(Andrew) Hwa S Lee
(74) *Attorney, Agent, or Firm*—Lumen Patent Firm

(57) ABSTRACT

Improved ease of mode matching to a passive optical cavity is provided by selecting a cavity design that has a predetermined deviation from a reference cavity design having high transverse mode degeneracy. This predetermined deviation tends to be small, so that the first overlap of high-order transverse modes with the lowest order transverse mode in frequency occurs at relatively high transverse mode numbers. Coupling to high-order transverse modes is thereby reduced, since high-order transverse modes having relatively high transverse mode numbers tend to be more difficult to couple to, and tend to have high loss. During assembly of such a cavity, it can be useful to apply a perturbation to the cavity to further optimize mode matching. For example, the length of an enclosed cavity can be adjusted by altering the number and/or length of spacers in the cavity housing.

5 Claims, 4 Drawing Sheets

CAVITY ENHANCED OPTICAL SPECTROSCOPY WITH A CAVITY HAVING A PREDETERMINED DEVIATION FROM A MODE DEGENERACY CONDITION

CROSS REFERENCE TO RELATED APPLICATIONS

This application claims the benefit of U.S. provisional patent application 60/776,396, filed on Feb. 23, 2006, entitled "Methods and Apparatus for Improved Cavity Ring-down Spectroscopy", and hereby incorporated by reference in its entirety.

FIELD OF THE INVENTION

This invention relates to cavity enhanced spectroscopy and cavity enhanced absorption spectroscopy.

BACKGROUND

Optical spectroscopy entails passing optical radiation through a sample, often referred to as an analyte, and inferring properties of the analyte from measurements performed on the optical radiation. For example, trace gas detection can be spectroscopically performed by performing measurements to detect the presence or absence of spectral absorption lines corresponding to the gas species of interest. Optical spectroscopy has been intensively developed over a period of many decades, and various ideas have been developed to improve performance.

One such idea can be referred to as cavity-enhanced spectroscopy, in which the analyte is disposed within an optical cavity (i.e., an optical resonator). The cavity can enhance the interaction between the analyte and the optical radiation, thereby improving spectroscopic performance. For example, in cavity ring-down spectroscopy (CRDS), a form of cavity enhanced absorption spectroscopy, the absorption is measured by way of its effect on the energy decay time of an optical cavity. Increased absorption decreases the decay time, and vice versa. As another example, cavity enhanced absorption spectroscopy (CEAS) can also be employed to increase the sensitivity of absorption spectroscopy in connection with direct absorption measurements.

A significant alignment issue faced in many implementations of cavity-enhanced spectroscopy is selectively exciting the lowest order transverse mode of a passive optical cavity with an external optical source while minimizing excitation of the higher order transverse modes of the cavity. The theoretical condition for providing such selective mode excitation is well known in the art, and is often referred to as "mode matching". For example, suppose radiation in the lowest order transverse mode of an optical cavity would be emitted from the cavity as a Gaussian beam having certain parameters (e.g., waist size $w_0$, waist position $z_0$) along a beam axis L. In this example, radiation provided to the cavity as a Gaussian beam with waist size $w_0$ and waist position $z_0$ along beam axis L is mode matched to the lowest order transverse mode of the resonator, and will selectively excite the lowest order transverse mode of the cavity.

In experimental practice, mode matching is often optimized by monitoring the excitation of the higher order transverse modes, and by adjusting the system to minimize such excitation. For example, the spatial mode pattern can be monitored, or a fast detector can be employed to monitor transverse mode beating. In an article by Lee et al. entitled "Optimization of the mode matching in pulsed cavity ring-down spectroscopy by monitoring non-degenerate transverse mode beating" (Appl. Phys. B 74 435-440 (2002)), mode matching is optimized by introducing an intentional misalignment of a degenerate cavity. Such misalignment breaks the mode degeneracy, and results in transverse mode beating at relatively low frequencies, which do not require a fast detector to measure. Mode matching to the cavity is optimized by minimizing the amplitude of the slow mode beating, and then the misalignment is removed to complete alignment.

Despite the use of such methods for optimizing mode matching, it remains difficult and/or time consuming to optimize mode matching in practice. Accordingly, it would be an advance in the art to provide improved ease of mode matching to an optical cavity.

SUMMARY

Improved ease of mode matching to a passive optical cavity is provided by selecting a cavity design that has a predetermined deviation from a reference cavity design having high transverse mode degeneracy. This predetermined deviation tends to be small, so that the first overlap of high-order transverse modes with the lowest order transverse mode in frequency occurs at relatively high transverse mode numbers. Coupling to high-order transverse modes is thereby reduced, since high-order transverse modes having relatively high transverse mode numbers tend to be more difficult to couple to, and tend to have high loss. During assembly of such a cavity, it can be useful to apply a perturbation to the cavity to further optimize mode matching. For example, the length of an enclosed cavity can be adjusted by altering the number and/or length of spacers in the cavity housing.

DETAILED DESCRIPTION

Figure 1:
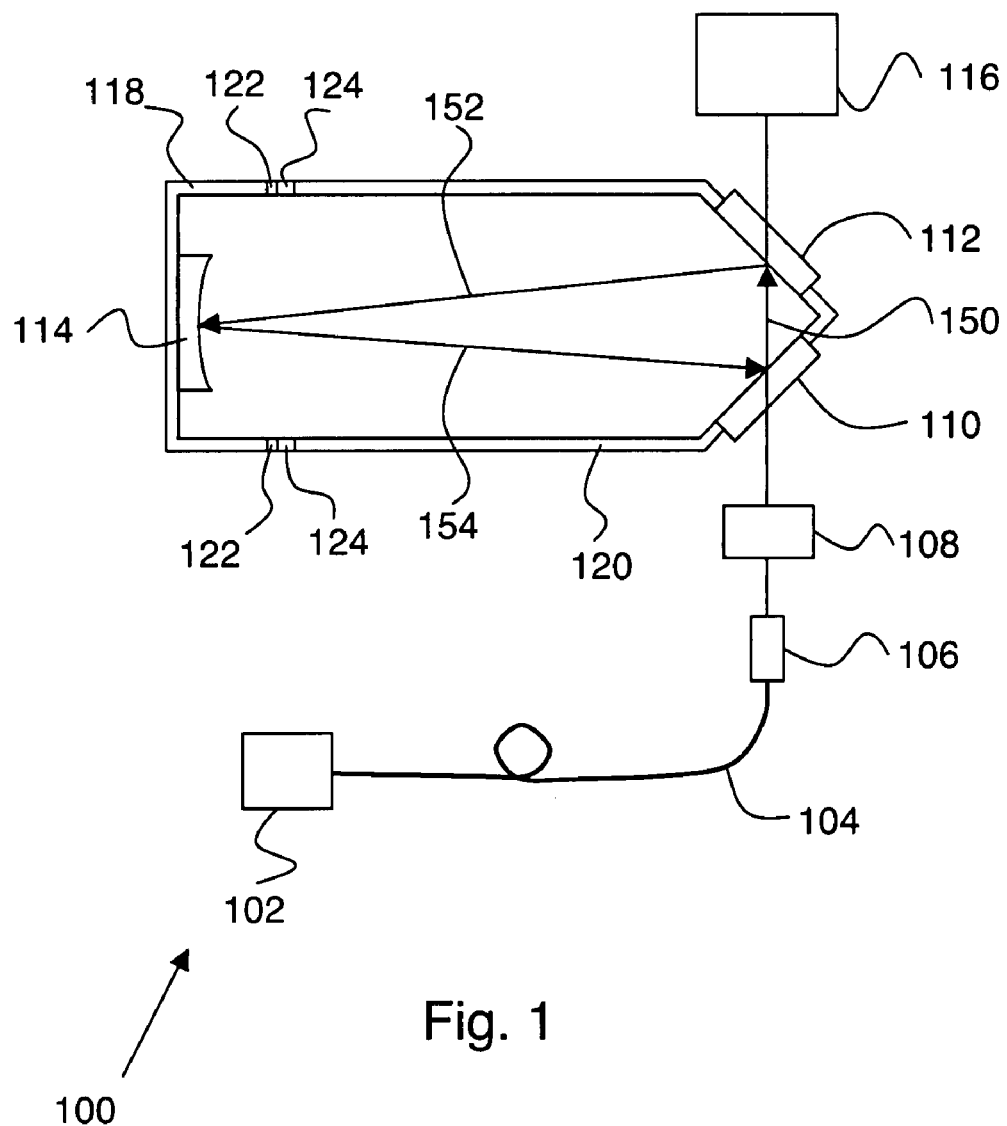
FIG. 1 shows a cavity-enhanced spectroscopy system according to an embodiment of the invention.

FIG. 1 shows a cavity-enhanced spectroscopy system 100 according to an embodiment of the invention. In this example, a source 102 is coupled to a fiber 104 which terminates in a fiber collimator 106. Radiation emitted from fiber collimator 106 passes through mode matching optics 108 and is coupled into an optical cavity formed by mirrors 110, 112, and 114. This optical resonator is a ring resonator having a round trip path along segments 150, 152, and 154. Radiation emitted from the cavity is detected by a detector 116.

Preferably, the cavity mirrors are included in an enclosed housing having a length that can be adjusted during assembly and fixed thereafter. For example, the configuration of FIG. 1 shows a front housing 120 to which mirrors 110 and 112 are affixed, and a back housing 118, to which mirror 114 is affixed. Spacers 122 and 124 are disposed between front housing 120 and back housing 118. The cavity length can be altered during assembly by changing the number and/or length of the spacers. In this way, cavity length adjustment can be provided for an enclosed cavity. Enclosed cavities are desirable for certain applications (e.g., measuring a gas sample at non-atmospheric and/or variable pressure). The purpose of including this degree of freedom during assembly is described below.

As indicated above, the invention relates mainly to the cavity design. Accordingly, practice of the invention does not depend on details of the source and detector configuration, and these aspects are shown on FIG. 1 for illustrative purposes.

Instead, the invention relates mainly to controlling the transverse mode distribution of the cavity by appropriate design methods. Accordingly, it is helpful to consider the mode spectrum of a two mirror cavity having length L and mirror radii of curvature $R_1$ and $R_2$. This mode spectrum is given by $$\omega_{qnm} = \frac{\pi c}{L}\left[q + (n + m + 1)\frac{\cos^{-1} \pm \sqrt{g_1 g_2}}{\pi}\right], \quad (1)$$

where q is the longitudinal number, n and m are the transverse mode numbers, $g_1=1-L/R_1$, and $g_2=1-L/R_2$. Here, the + sign applies if $g_1 \geq 0$ and $g_2 \geq 0$, and the − sign applies if $g_1 \leq 0$ and $g_2 \leq 0$ (see e.g., Lasers by Siegman, p. 762). It is also helpful to define $$d = \frac{\cos^{-1} \pm \sqrt{g_1 g_2}}{\pi}, \quad (2)$$

which allows the mode spectrum to be expressed as $$\omega_{qnm} = \frac{\pi c}{L}[q + (n + m + 1)d]. \quad (3)$$

The parameter d satisfies the relation $0 \leq d \leq 1$. The free spectral range (FSR) is the longitudinal mode spacing, and in this example the FSR is $\pi c/L$. The transverse mode spacing is dFSR, so the parameter d can be understood as the transverse mode spacing, normalized to the FSR.

Figure 2:
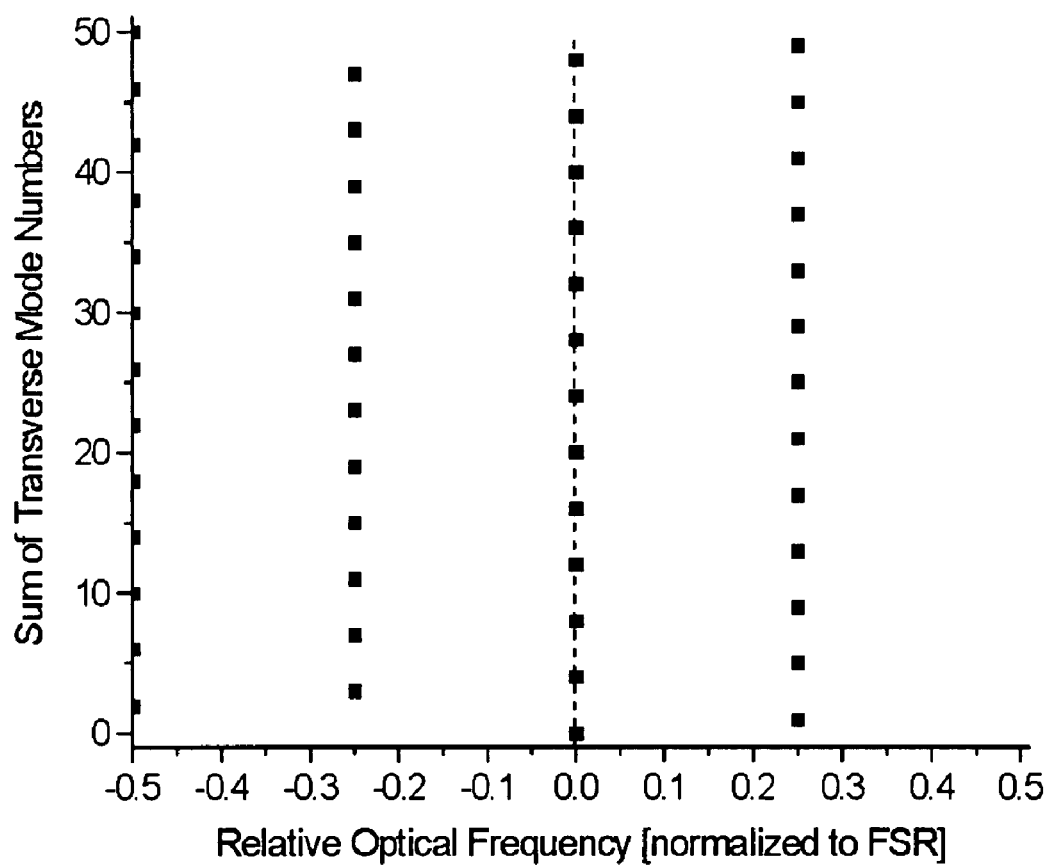
FIG. 2 is an exemplary plot of mode frequencies vs. transverse mode number sum for a highly degenerate cavity design.

For certain values of d, the resulting cavity has a highly degenerate mode spectrum. FIG. 2 is an exemplary plot of mode frequencies vs. transverse mode number sum for a highly degenerate cavity design. This example relates to a semi-confocal cavity ($R_1$=infinity, $R_2$=2L), which gives d=¼. The horizontal axis of FIG. 2 shows mode frequencies modulo normalized to a free spectral range, and the vertical axis is transverse mode number sum (i.e., n+m). Modulo normalization to an FSR means that the squares in each column have frequencies that differ among each other by an integer number of FSRs. The pattern of frequency degeneracy shown on such a normalized frequency scale is the same pattern as on a physical frequency scale, since equality of all frequencies in each column can be provided by appropriate assignments of the longitudinal mode numbers (q). As the transverse mode number sum increases, only 4 mode frequencies ever occur within each FSR, spaced apart by ¼ of the FSR. Thus any particular mode frequency is highly degenerate, since many different modes share the same frequency. For example, the TEM02, TEM11, and TEM20 modes all have the same frequency which is separated by FSR/2 from the TEM00 frequency.

In particular, many different transverse modes share the same frequency as the desired TEM00 lowest order cavity mode (i.e., the n+m=0 mode in FIG. 2), making selective excitation of the TEM00 mode undesirably difficult. More specifically, relatively low-order transverse modes (e.g., n+m=4) coincide in frequency with the desired TEM00 mode, which is particularly undesirable since such relatively low-order modes tend to be easy to excite and tend to have low losses, comparable to but slightly different from the loss of the TEM00 mode. Thus the presence of such modes tends to be particularly harmful to spectroscopic performance.

Figure 3:
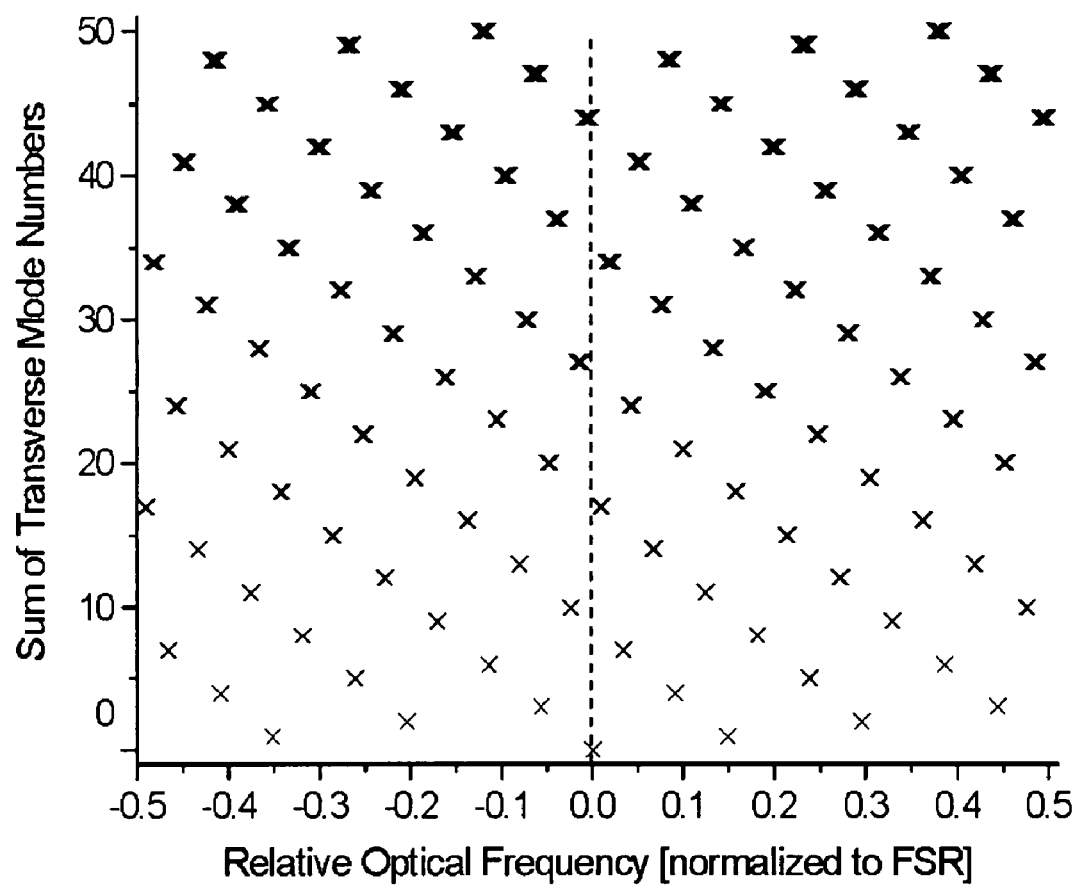
FIG. 3 is an exemplary plot of mode frequencies vs. transverse mode number sum for a typical three mirror cavity design having astigmatism.

FIG. 3 is an exemplary plot of mode frequencies vs. transverse mode number sum for a typical three mirror cavity design. In this example, two closely spaced planar mirrors (spacing about 1 cm) are positioned at slightly less than a 90-degree angle with respect to each other, where both planar mirrors face a concave mirror (e.g. 100-cm radius of curvature) positioned some distance away (e.g., 20 cm). Such a cavity is similar to the cavity shown in FIG. 1. To first order, such a cavity can be analyzed as if it were a two-mirror cavity, since two of the mirrors are planar, and the curved mirror is at nearly normal incidence. For this example, the cavity design is not highly degenerate, and many mode frequencies are present in each FSR range. In this example, overlaps with the lowest order mode occur at about n+m=17, 35 and 45. Although this is an improvement compared to the highly degenerate case, frequency overlap still occurs at an undesirably low transverse mode sum (i.e., n+m=17).

Off normal incidence at incidence angle $\theta_i$ on the concave mirror can be modeled by considering decreasing the mirror radius of curvature (ROC) in the plane of incidence by a factor of $\cos(\theta_i)$ and by increasing the ROC in the plane perpendicular to the plane of incidence by a factor of $1/\cos(\theta_i)$. The resulting astigmatism breaks the symmetry between the transverse mode numbers n and m seen in Eqs. 1-3. For example, the degeneracy between TEM20, TEM11 and TEM02 mode frequencies is broken by astigmatism. The detailed calculations performed for FIG. 3 account for this astigmatism, and as a result the mode frequencies at higher n+m are shown as spread out horizontally. Intentional or unintentional perturbations to the cavity can also lead to horizontal spreading as in FIG. 3.

Another factor to consider in three mirror cavities is that the odd number of mirrors causes a reversal of the beam image in the plane of reflection on each round trip. As a result of this effect, the frequencies of transverse modes having odd mode numbers are shifted by FSR/2 relative to what they would be in a standing-wave cavity which lacks the image reversal.

Figure 4:
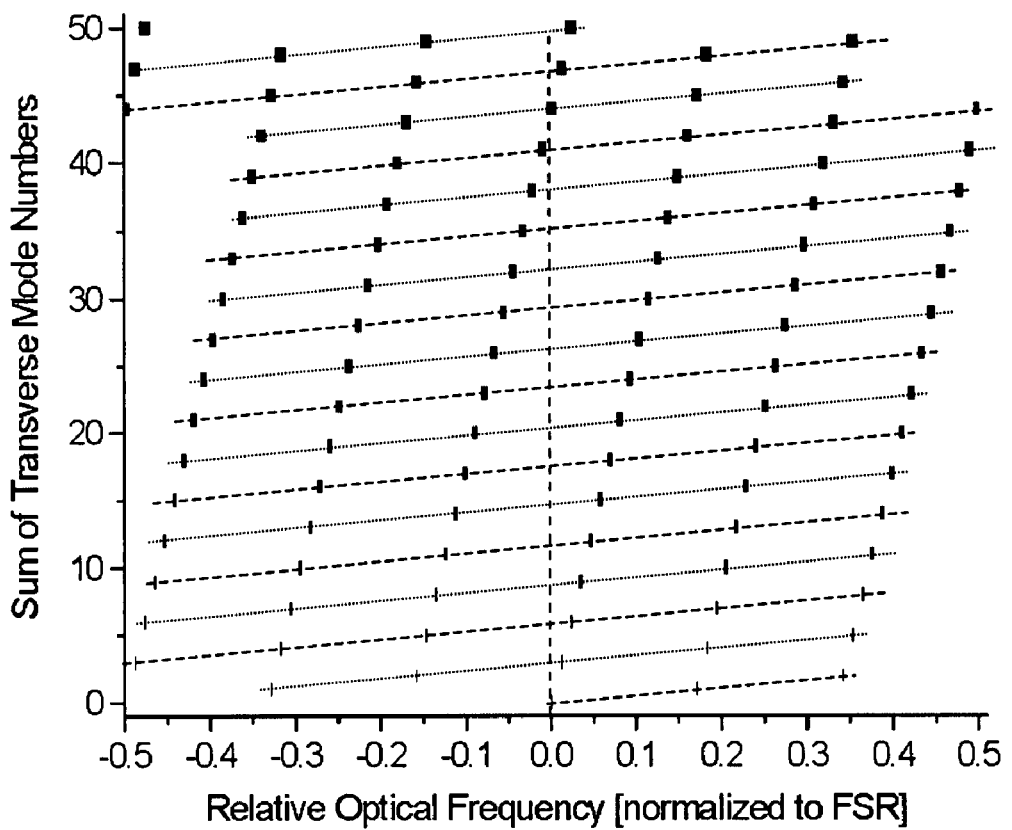
FIG. 4 is an exemplary plot of mode frequencies vs. transverse mode number sum for a cavity according to an embodiment of the invention.

FIG. 4 is an exemplary plot of mode frequencies vs. transverse mode number sum for a cavity according to an embodiment of the invention. This example is a three mirror cavity having two closely spaced planar mirrors and a concave mirror of radius R spaced nearly L=R/4 away from the midpoint between the planar mirrors as measured along the optical beam path. More specifically, if a two-mirror cavity having d=⅙ is regarded as a reference cavity design, the cavity design of FIG. 4 has a predetermined deviation of about 2% from this reference cavity design (i.e., d=0.98(⅙)).

As a result of this deviation, the resulting mode frequencies do not line up vertically at the FSR/6 frequencies (e.g., as on FIG. 2). Instead, there is a diagonal pattern, where the vertical arrangement of mode frequencies seen on FIG. 2 is slightly tilted. As a result of this relatively small tilt, the first mode that coincides in frequency with the lowest order transverse mode has a relatively high transverse mode number sum (about 45 in this example). This situation is highly desirable for selective excitation of the lowest order transverse mode, since higher-order modes having such high transverse mode number sum tend to have high loss and tend to be more difficult to excite than higher-order modes having lower transverse mode number sums.

As in FIG. 3, the effect of cavity astigmatism is included in the calculations of FIG. 4, resulting in a horizontal broadening of the cavity mode frequencies at higher transverse mode number sums. Since the example of FIG. 4 is a three mirror cavity, some of the modes are shifted in frequency by FSR/2, as described above. As a result of this shift, two interleaved sets of modes are present on FIG. 4, shown with dotted and dashed lines respectively. Within each set of modes, the smooth progression expected for d about equal to ⅙ is apparent.

In view of these considerations, the following cavity design approach has been developed, in accordance with principles of the invention.

First, a reference optical cavity design is selected. The reference optical cavity design provides a highly degenerate mode spectrum. More specifically, the reference optical cavity design provides a mode spacing that is a small integer fraction of the free spectral range. Suitable small integer fractions include, but are not limited to ⅙, ⅕, ¼, ⅓, ½, 1, 0, ⅖, ⅔, ⅗, ¾, ⅘, and ⅚. Many commonly employed cavity designs are highly degenerate, such as planar, spherical, confocal and semi-confocal cavities. Such cavities can have two mirrors, or three or more mirrors. Cavities having two or more mirrors can be configured as standing wave resonators or ring resonators. A two-mirror ring cavity can include polarization-rotating optics to provide orthogonal polarizations (e.g., horizontal and vertical) for the forward and backward passes through the cavity.

Second, an actual cavity design having a predetermined and non-zero deviation away from the reference optical cavity design is selected. If this deviation is too small, the resulting cavity is too close to the highly degenerate condition (e.g., as shown on FIG. 2), and astigmatism or other perturbations may result in the actual cavity being highly degenerate, which is undesirable. If this deviation is too large, then the first higher-order transverse mode that coincides in frequency with the TEM00 mode may have an undesirably low transverse mode sum (e.g., as in FIG. 3). It is convenient to define $d_a = d_0 + \Delta d$, where $d_0$ is the d factor for the reference cavity design (i.e., a small integer faction), $d_a$ is the d factor for the actual cavity design, and $\Delta d$ is the difference between the two. It is also convenient to define $d_0 = d_n/d_d$, where $d_n$ and $d_d$ are non-negative integers having no common factor.

From Eq. 3, the lowest transverse mode sum at which a frequency overlap with the TEM00 mode occurs satisfies $(n+m)|\Delta d| = d_d$. The change in frequency caused by $\Delta d$ is $(n+m)|\Delta d|$, and the frequency shift needed to cause an overlap is $d_d$, because the mode pattern for the reference cavity design has vertical columns spaced by $d_d$. For example, if $d_0 = \frac{5}{6}$, then the mode pattern has 6 columns in each FSR range. We have found that it is preferable to require $n+m \geq 20$ for the first mode frequency overlap in practice, which implies $|\Delta d|/d_d$ is preferably $\leq 0.05$. Another factor to consider in setting the lower limit on $|\Delta d|$, in addition to keeping a suitable margin relative to the highly degenerate reference cavity design, is that the spreading of mode frequencies due to astigmatism increases as transverse mode number sum increases. At a sufficiently high mode number sum $M_0$, the gaps between the clusters of mode frequencies disappear entirely (i.e., the discrete horizontal bars on FIG. 4 merge). There is little value in attempting to set $|\Delta d|$ so low as to provide a first overlap $n+m > M_0$, since $M_0$ is effectively an upper limit for the first overlap mode number. In view of typical levels of cavity astigmatism, and to avoid coming too close to the highly degenerate cavity situation, it is preferable for $|\Delta d|/d_d$ to be $\geq 0.01$. The deviation of $d_a$ from $d_0$ can have either sign, so the preceding inequalities relate to the magnitude $|\Delta d|$ of $\Delta d$.

Once the deviation $\Delta d$ is thus predetermined, the actual cavity design is such that the mode spectrum has a first mode overlap at a relatively high transverse mode number sum (preferably this sum >20), which is advantageous as described above. Once the actual cavity $d_a$ is known, any combination of cavity parameters (e.g., L, $R_1$, $R_2$ for a two mirror cavity) providing this value of $d_a$ is suitable for practicing the invention. The actual cavity design can also differ from the reference cavity design in other ways that do not significantly affect this aspect of the mode spectrum. For example, the reference cavity can be a two-mirror cavity, and the actual cavity can be a three-mirror cavity designed to approximate a two-mirror cavity having the selected deviation $d_a$.

In some cases, adequate results can be obtained by assembly of a cavity having the predetermined deviation $\Delta d$ from the reference cavity design with conventional cavity assembly techniques. However, in many cases, it is helpful to perform one-time adjustments during assembly to optimize mode matching performance. One particularly convenient cavity parameter to adjust during assembly for this purpose is cavity length (e.g., with spacers as described in connection with FIG. 1). The number and/or length of spacers can be adjusted during assembly to minimize the observed excitation of higher-order transverse modes during a test procedure. Once the best combination of spacers is determined, the spacers are affixed into position.

Parameters of the cavity other than length can also be perturbed (or "tweaked") during cavity assembly as one-time adjustments to optimize mode matching performance. Suitable perturbations include, but are not limited to: cavity mirror rotation, cavity mirror translation, changing cavity length, changing a stress applied to a cavity optical element, and changing cavity axis alignment. For example, rotation or translation of mirrors prior to gluing can alter the position of the illuminated spot on the mirrors. Squeezing the side of a mirror while gluing it down can set a stress on the mirror. Changing the cavity axis alignment can be done by tilting planar mirrors and/or by translating curved mirrors. For a three-mirror cavity as in FIG. 1, it is preferable to translate the curved mirror to adjust cavity axis alignment. The back mirror assembly can also be rotated to change cavity axis alignment, since such rotation is likely to be away from the cavity axis-normal to the back mirror. Preferably, the back mirror assembly has both translational and rotational degrees of freedom during assembly.

The invention claimed is:

1. A method of making an apparatus for cavity enhanced optical spectroscopy, the method comprising:

providing a source of optical radiation capable of emitting source radiation;

providing an optical resonator having a lowest order resonator transverse mode and having multiple other resonator transverse modes, wherein the source radiation is coupled to the lowest order resonator transverse mode;

providing a detector capable of receiving radiation emitted from the optical resonator;

providing a reference optical resonator design having mode frequencies spaced by a small integer fraction of a free spectral range of said reference optical resonator, wherein said small integer fraction is selected from the group consisting of: 1/6, 1/5, 1/4, 1/3, 1/2, 1, 0, 2/5, 2/3, 3/5, 3/4, 4/5, and 5/6;

deriving a design for said optical resonator by making a predetermined and non-zero deviation away from the reference optical resonator design.

2. The method of claim 1, further comprising selecting said predetermined deviation according to a method comprising:

defining FSR as a free spectral range of said optical resonator;

defining doFSR as a transverse mode frequency spacing of said reference optical resonator design;

defining daFSR as a transverse mode frequency spacing of said design of said optical resonator;

defining $\Delta d = d_a - d_0$ to be said predetermined deviation;

defining $d_n$, and $d_d$ to be nonnegative integers having no common factor and satisfying $d_0 = d_n/d_d$;

selecting said predetermined deviation to be in a range given by $0.01 \leq |\Delta d|/d_d \leq 0.05$.

3. The method of claim 1, wherein said reference optical resonator design is a three mirror design.

4. The method of claim 1, further comprising applying one or more perturbations to said optical resonator during assembly to minimize measured excitation of said higher order modes during assembly test.

5. The method of claim 4, wherein said one or more perturbations are selected from the group consisting of: cavity mirror rotation, cavity mirror translation, changing cavity length, changing a stress applied to a cavity optical element, and changing cavity axis alignment.

* * * * *